US00PP28401P3

(12) United States Plant Patent
Swartz et al.

(10) Patent No.: US PP28,401 P3
(45) Date of Patent: Sep. 19, 2017

(54) RASPBERRY PLANT NAMED 'ADDISON'

(50) Latin Name: ***Rubus idaeus* L.**
Varietal Denomination: Addison

(71) Applicant: FIVE ACES BREEDING LLC, Oakland, MD (US)

(72) Inventors: Harry Jan Swartz, Oakland, MD (US); Benjamin Dale Stokes, Wilmington, DE (US)

(73) Assignee: Five Aces Breeding LLC, Oakland, MD (US)

( * ) Notice: Subject to any disclaimer, the term of this patent is extended or adjusted under 35 U.S.C. 154(b) by 61 days.

(21) Appl. No.: 14/757,290

(22) Filed: Dec. 15, 2015

(65) Prior Publication Data

US 2017/0172036 P1 Jun. 15, 2017

(51) Int. Cl.
*A01H 5/08* (2006.01)

(52) U.S. Cl.
USPC ..... Plt./204

(58) Field of Classification Search
USPC ..... Plt./204
See application file for complete search history.

(56) References Cited

U.S. PATENT DOCUMENTS

PP6,597 P 2/1989 Keep
PP7,067 P 12/1989 Sanford et al.
PP10,411 P 5/1998 Swartz et al.
PP10,412 P 5/1998 Swartz et al.
PP10,610 P 9/1998 Swartz et al.
PP11,747 P2 1/2001 Sanford et al.
PP12,173 P2 10/2001 Swartz et al.
PP12,350 P2 1/2002 Swartz et al.
PP15,647 P2 3/2005 Swartz et al.
PP21,007 P3 5/2010 Swartz
PP21,185 P3 8/2010 Hall et al.
PP23,375 P3 2/2013 Weber
PP24,949 P3 10/2014 Weber

OTHER PUBLICATIONS

Department of Agriculture Sixteenth Annual Report of the Board of Control of the New York Agricultural Experiment Station for the Year 1897 (1898) p. 290.*

* cited by examiner

*Primary Examiner* — June Hwu
(74) *Attorney, Agent, or Firm* — Rosenberg, Klein & Lee

(57) ABSTRACT

The present invention is a new and distinct primocane and floricane fruiting red raspberry cultivar named 'Addison', which is capable of producing high yields of medium large, dark red, flavorful and firm fruit that are easy to harvest. The cultivar is also characterized by several morphological characteristics, including, a strong tendency toward red coloration of vegetative plant parts, bracts on peduncles, a long necked receptacle, and a slight imperfection of the fruit which can produce flattened surfaces.

9 Drawing Sheets

Figure 1:
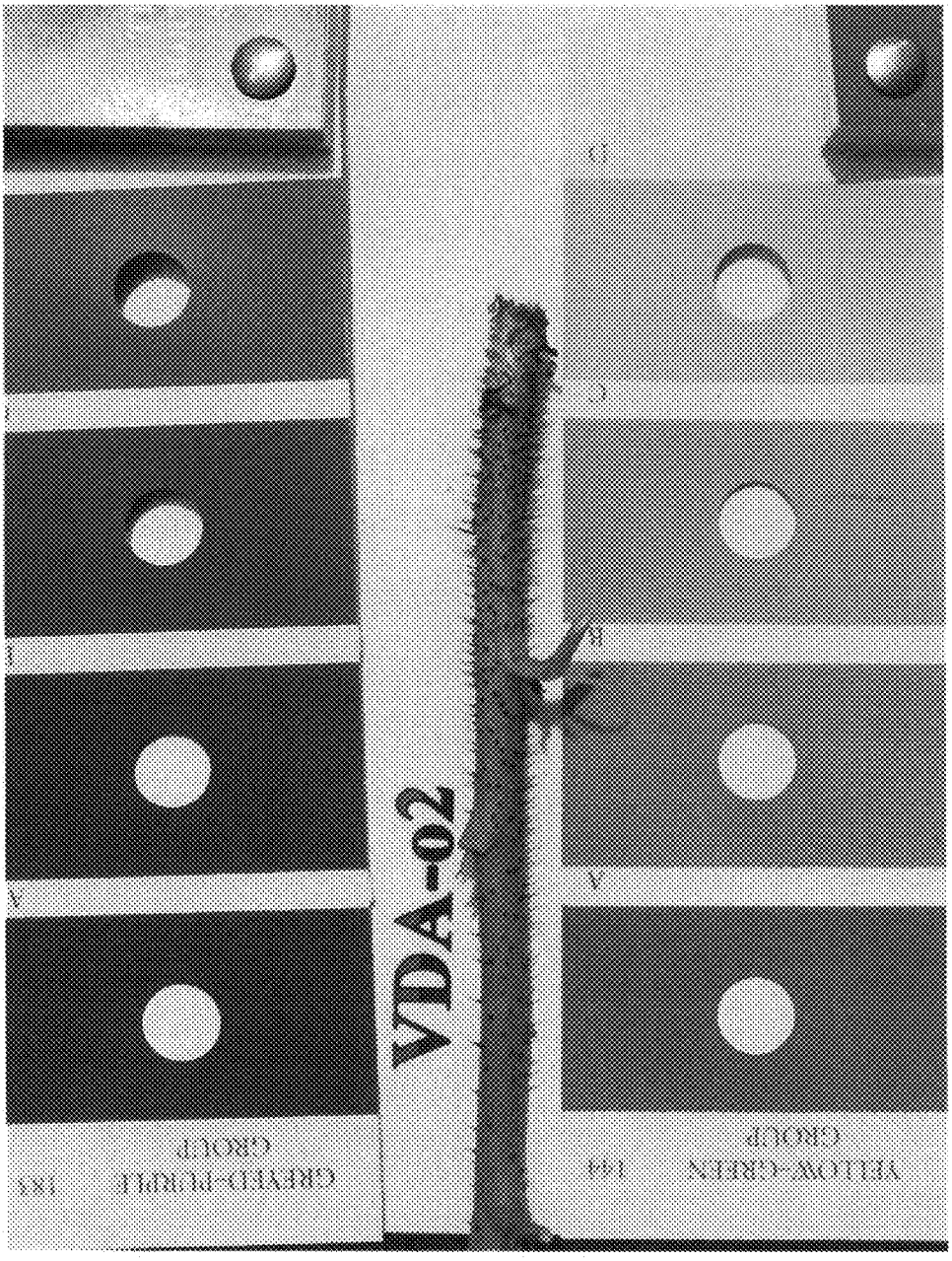

Latin name of the genus and species: *Rubus idaeus* L.
Variety denomination: 'Addison'.

FIELD OF THE INVENTION

This invention concerns a new and distinct cultivar of late summer to fall primocane and late spring to summer floricane fruiting raspberry plant with a botanical name of *Rubus idaeus* L. The new cultivar is distinguished from other cultivars by its dark red fruit; by its combination of fruit firmness, high sugar levels, ease of picking and size; several growth characteristics; and productivity in two seasons. 'Addison' is thereby suitable for regional, commercial, premium fresh fruit marketing and local or on farm marketing.

DESCRIPTION OF RELATED PRIOR ART

Several cultivars of dark colored red raspberry fruit are known. The present invention, 'Addison' fruit is dark colored in appearance. Fully fruit ripens to 2001 Royal Horticultural Society Colour Plate No. 46A and remains on the plant until overripe and darker red color, reminiscent of 2001 Royal Horticultural Society Colour Plate No. 59A at overripe. 'Caroline' (U.S. Plant Pat. No.10,412) and 'Crimson Giant' (U.S. Plant Pat. No. 23,375) fruit, other dark colored fruit, ripen with 2001 Royal Horticultural Society Colour Plate No. 45A and 46A. 'Wakefield' (U.S. Plant Pat. No. 21,185) and 'Jaclyn' (U.S. Plant Pat. No. 15,647), two additional dark colored fruiting red raspberry cultivars, have a similar color to 'Addison', reminiscent of 2001 Royal Horticultural Society Colour Plates No. 59A and N77 when ripe and overripe. 'Meeker' (unpatented) fruit is similar to 'Wakefield' (U.S. Plant Pat. No. 21,185) in coloration. 'Crimson Night' (U.S. Plant Pat. No. 24,949) fruit ripens slightly darker. Of the above dark fruited cultivars, only 'Addison', 'Crimson Giant' (U.S. Plant Pat. No. 23,375) and 'Caroline' (U.S. Plant Pat. No. 10,412) are both spring and fall fruiting. 'Wakefield' (U.S. Plant Pat. No. 21,185) and 'Meeker' are exclusively spring (floricane) fruiting and 'Jaclyn' (U.S. Plant Pat. No. 15,647), 'Crimson Night' (U.S. Plant Pat. No. 24,949) and 'Crimson Giant' (U.S. Plant Pat. No. 23,375) plants are primocane fruiting. 'Addison' can be distinguished from 'Caroline' (U.S. Plant Pat. No. 10,412) in having larger, much firmer fruit on more vigorous canes. 'Addison' plants produce a lower number of canes than 'Caroline' (U.S. Plant Pat. No. 10,412). 'Addison' leaves do not regularly curl in high sun and warm temperatures as 'Caroline' (U.S. Plant Pat. No. 10,412). 'Addison' can be distinguished from 'Crimson Giant' (U.S. Plant Pat. No. 23,375) by season of fall cropping, which is much earlier in 'Addison'. 'Jaclyn' (U.S. Plant Pat. No. 15,647), another fall bearing, dark fruited, red raspberry with other species in its pedigree, like 'Addison'; can be distinguished from 'Addison' on fruit characteristics and harvest season. 'Jaclyn' (U.S. Plant Pat. No. 15,647) is a short statured, early fall season, very conic fruited cultivar. 'Addison' fruit is truncated conic and harvest occurs a month after 'Jaclyn' (U.S. Plant Pat. No. 15,647) on primocanes. 'Jaclyn' (U.S. Plant Pat. No. 15,647) does not produce a large spring crop, unlike 'Addison'. 'Addison' fruit is easy to remove unripe, 'Jaclyn' (U.S. Plant Pat. No. 15,647) fruit is difficult to pick when fully ripe. 'Crimson Night' (U.S. Plant Pat. No. 24,949) fruit are smaller than 'Addison' and ripen on primocanes approximately two to three weeks later than 'Addison'.

ORIGIN OF THE NEW CULTIVAR

The new cultivar of red raspberry, 'Addison', originated from a controlled cross in Winter in a screened glasshouse in College Park, Md. The cross, designated: "DA" is a cross of the parents SDO-1 (female—unpatented)×RH-5 (male—unpatented). Unlike 'Addison', SDO-1 has truncated conic, soft, fruit which is produced only on floricanes. While it is productive, like 'Addison', it lacks the dark vegetative coloration of 'Addison'. SDO-1 is a cross of ON-1 (female—unpatented)×'Emily' (male—U.S. Plant Pat. No. 12,350). ON-1 is a cross of HBK-5 (female—unpatented)×LA-2 (male—unpatented). HBK-5 is cross of 'Lauren' (female—U.S. Plant Pat. No. 10,610)×NY 817 (male—unpatented). LA-2 is a cross of *R. innominatus* S. Moore (female—wild species, unpatented)×'Glen Garry' (male—unpatented). RH-5, the pollen parent, is a very vigorous floricane only producer with small, soft, round fruit, unlike 'Addison'. RH-5 is a very vigorous cross of GEL-114 (female—unpatented)×NE-2 (male—unpatented). GEL-114 is a cross of 'Southland' (female—unpatented) by SCRI 86B16 (male—unpatented). NE-2 is a cross of FD-2 (female—unpatented)×'Emily' (male—U.S. Plant Pat. No. 12,350). FD-2 is a cross of *R. flos-culosis* Focke. (female—wild species, unpatented)×'Citadel' (male—unpatented).

The year of crossing was 2000; thus the year designation was "V". The seed from this cross were germinated in College Park, Md. and transported to the breeding field in Wilmington, Ohio where the seedlings were evaluated in 2003 and 2004. 'Addison' was the second selection of the VDA progeny in Ohio and was therefore designated "-o2". Thus, the complete breeding designation of 'Addison' is "VDA-o2". There are no synonyms for 'Addison'.

SUMMARY OF THE NEW CULTIVAR

This application relates to a new and distinct red raspberry cultivar, botanically known as *Rubus idaeus* L. The following characteristics are outstanding:

1. Production of high yields of medium large, firm, fruit in both the Spring on floricanes and Fall on primocanes.
2. The dark fruit has been determined to have high sugar levels, is storable, and is easy to harvest.
3. Unlike purple raspberries, which have similar dark fruit, the present invention does not have *Rubus occidentalis* L., the black raspberry, for at least four generations back in its pedigree.

These characteristics make 'Addison' suitable as a summer and fall fruiting type for premium fresh fruit marketing in commercial production areas worldwide. In cooler areas with less than 2500 growing degree days (base 50° F.), 'Addison' primocane fruit ripens in early August and through September, making it sufficiently early to use as a primocane bearer in unprotected culture for almost all agricultural regions in the United States.

The following characteristics are useful in distinguishing this cultivar from other cultivars and can be useful for cultivar identification. Plants used for these observations were grown in uncrowded conditions in clear plastic unshaded tunnels or greenhouses.

1. On newly established tissue culture propagated plants, 'Addison' plants produce primocanes which terminate in flower clusters within 5 months after planting. 'Addison' canes usually produce flowers at the $30^{th}$ node in pots in tunnels at 2900 ft. elevation in Maryland, United States. Buds subtending the $30^{th}$ node produce a full floricane crop in the following spring.
2. Ripe 'Addison' fruit is dark red in appearance reminiscent of 2001 Royal Horticultural Society Colour Plate No. 46A and remains on the plant until overripe and develops darker red color, reminiscent of 2001 Royal Horticultural Society Colour Plate No. 59A at overripe. After 7 days of storage at 40° F., fruit darkens to red purple reminiscent of 2001 Royal Horticultural Society Colour Plate No. 79A.
3. The vegetative above-ground portions of 'Addison' plants have a strong tendency to produce deep red color. Therefore, healthy canes, petioles, petiolules, peduncles, sepals and the base of major leaf veins will become red if exposed to full sun consistently. The extension of the color into the leaf veins is uncommon for raspberry and can be used to identify 'Addison' plants grown in full sun.
4. The flowering area on floricanes and primocanes have several monofoliolate leaves, as is common on some raspberry cultivars. 'Addison' peduncles also have reduced size, less than 1 cm. in length, monofoliolate leaves which look like bracts.
5. The fruit of 'Addison' has an imperfection on its collar, specifically, a drupelet will occasionally drop from the uniform basal row of drupelets to half way to the second row of drupelets. This imperfection causes the fruit to have an angular area when viewed from the base of a harvested fruit; that is, the cavity is not completely round or oval. This angle can cause a side of the fruit to be flattened. This imperfection does not cause fruit to crumble during harvest as the receptacle attachment to the fruit occurs only on the apical two thirds of its length. The imperfection occurs over the basal neck of the receptacle where no vascular attachment can stress the fruit during detachment.

BRIEF DESCRIPTION OF THE PHOTOGRAPHS

The accompanying photographs show typical characteristics of the new variety; the measuring stick is in numbered centimeters in FIGS. 2, 3, 6 and 8:

FIG. 1. shows a thorny 'Addison' young primocane section with 2001 Royal Horticultural Society Colour Plates No. 144 and 183.

Figure 2:
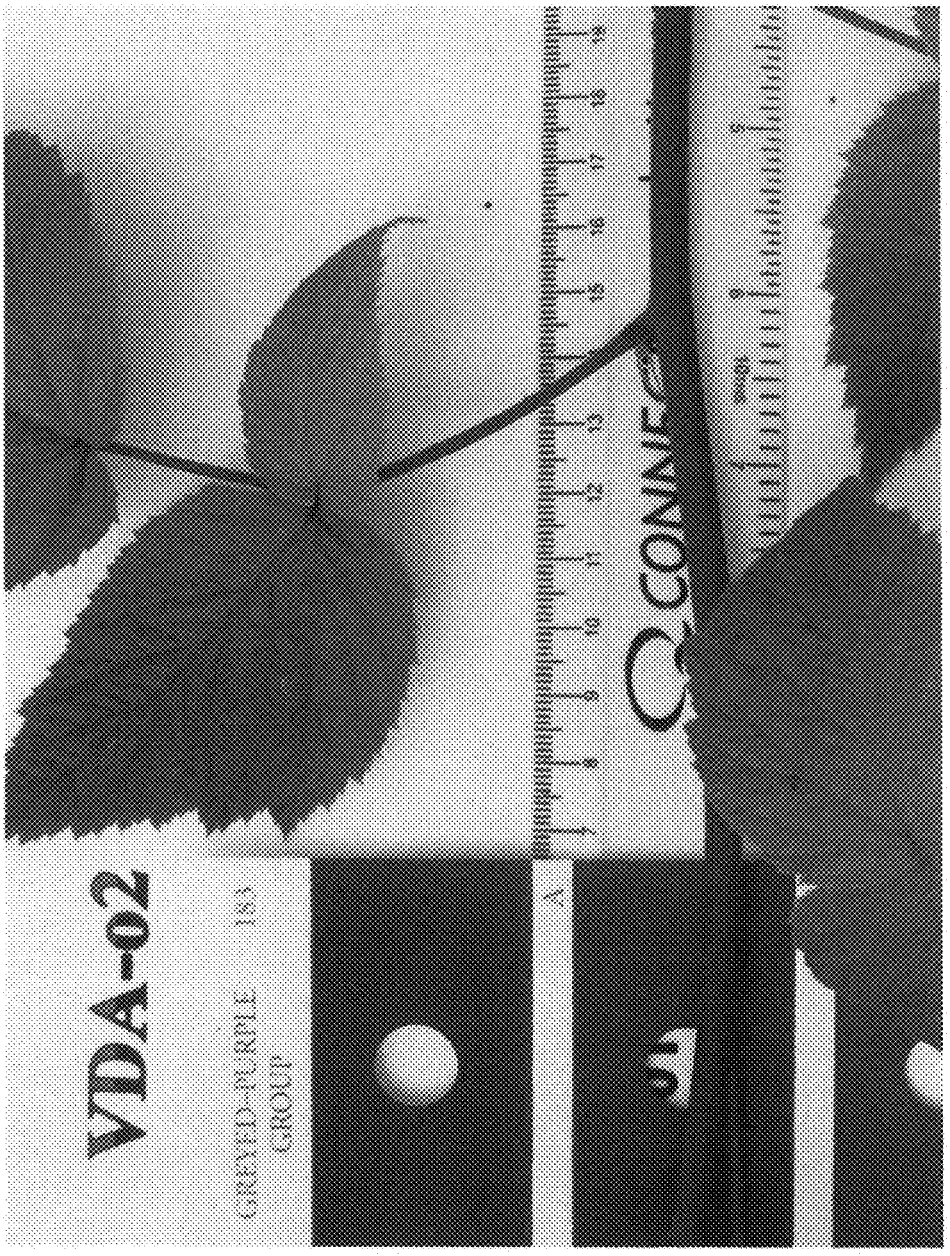

FIG. 2. shows the red blush on an 'Addison' primocane with 2001 Royal Horticultural Society Colour Plate No. 183.

Figure 3:
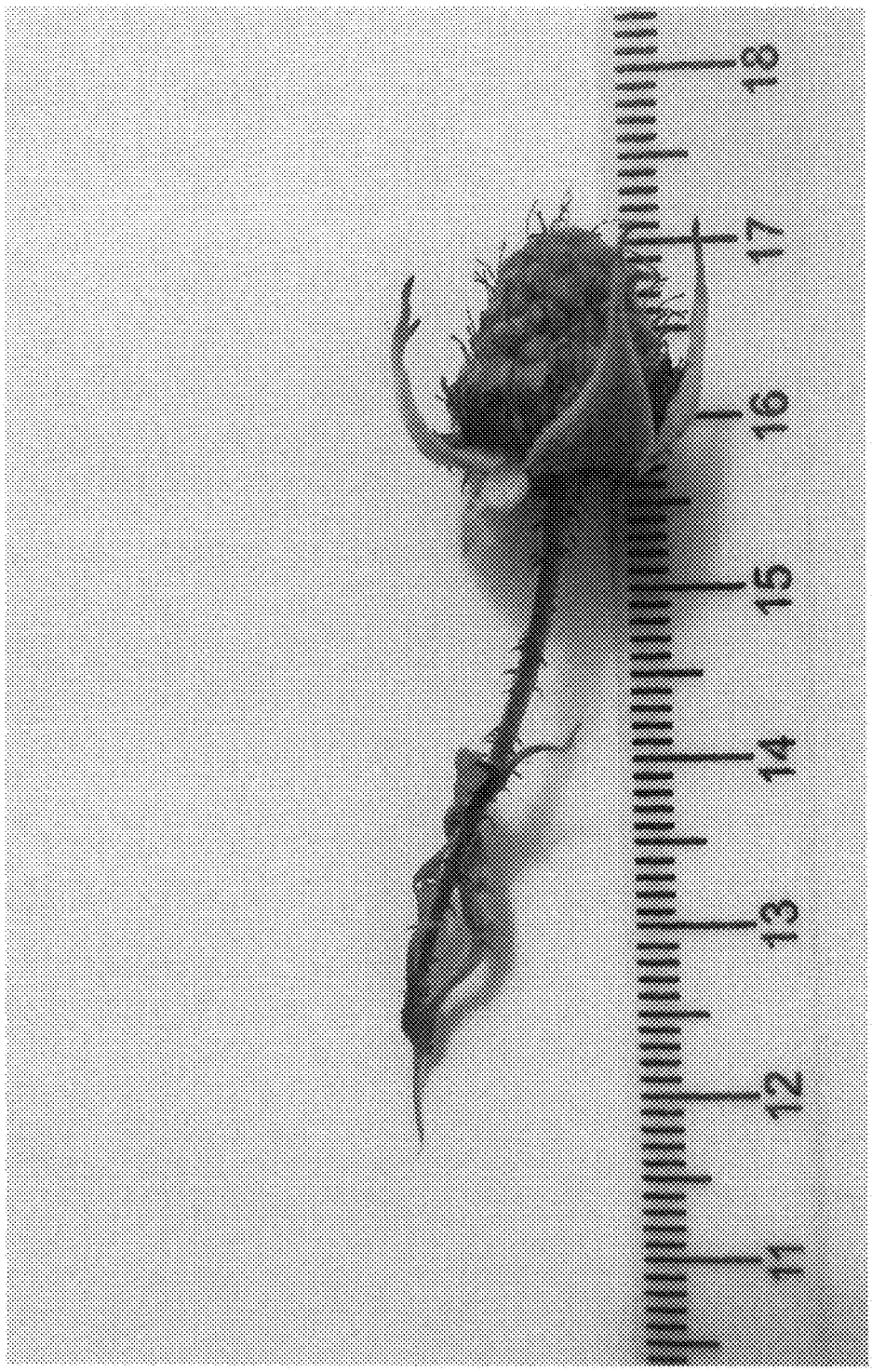

FIG. 3. shows an unripe fruit of 'Addison' with its peducle thorns and typic bracts or reduced size monofoliolate leaves.

Figure 4:
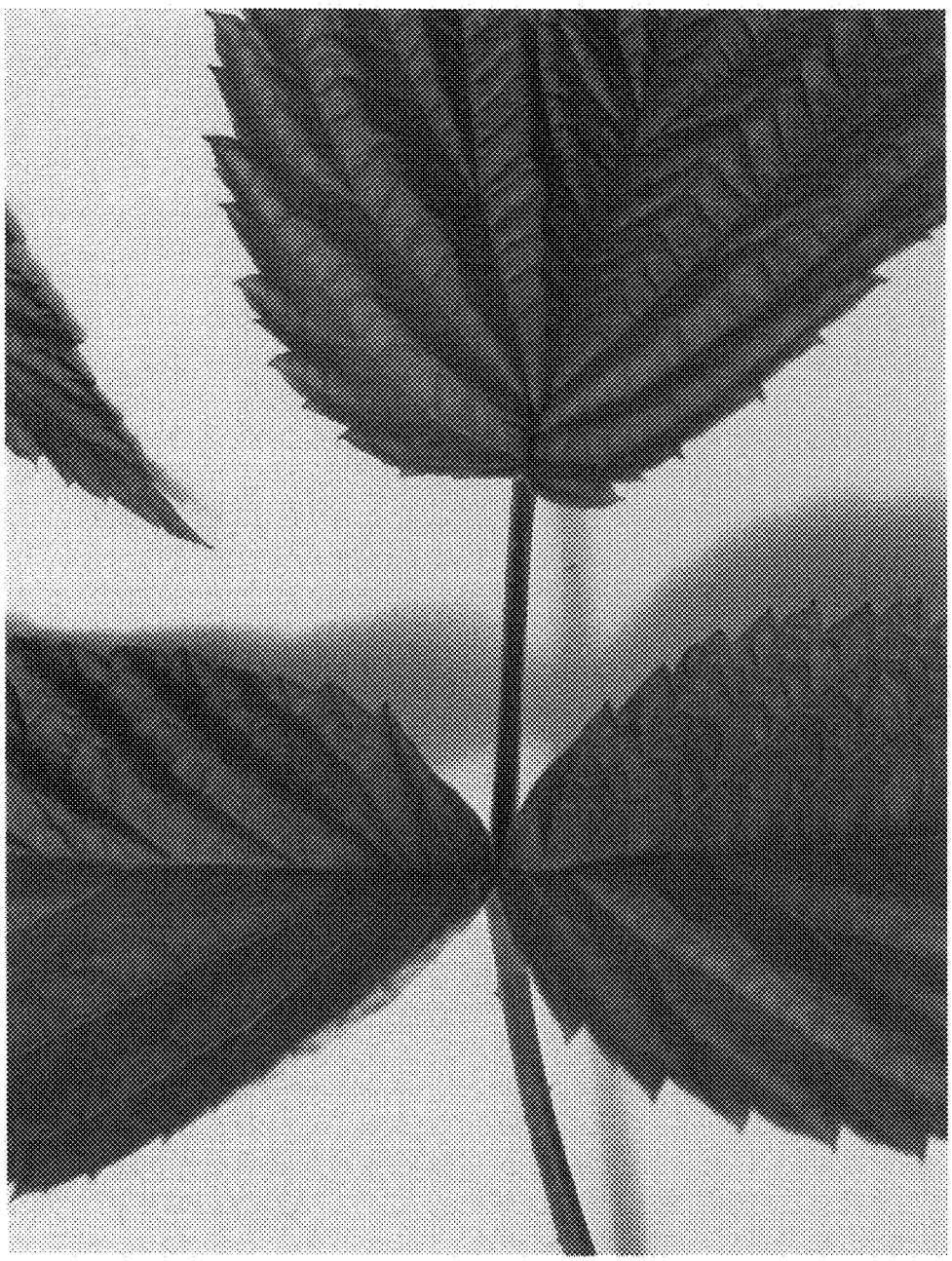

FIG. 4. shows the coloration of the upper surface of the midrib of an 'Addison' leaf.

Figure 5:
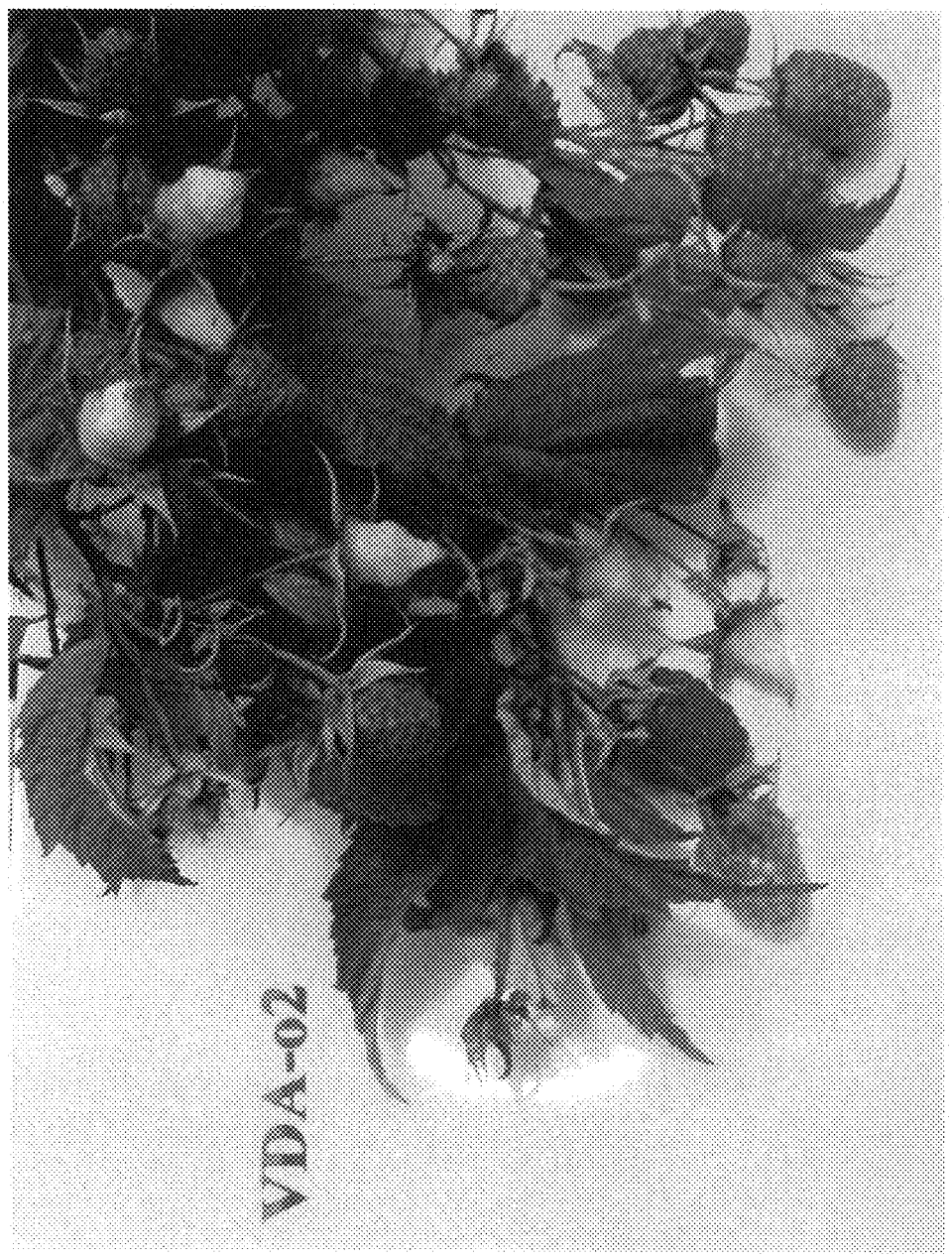

FIG. 5. shows the apical third of the flowering and fruiting section of an 'Addison' primocane and the relatively long receptacle neck where no vascular connections attach to the fruit.

Figure 6:
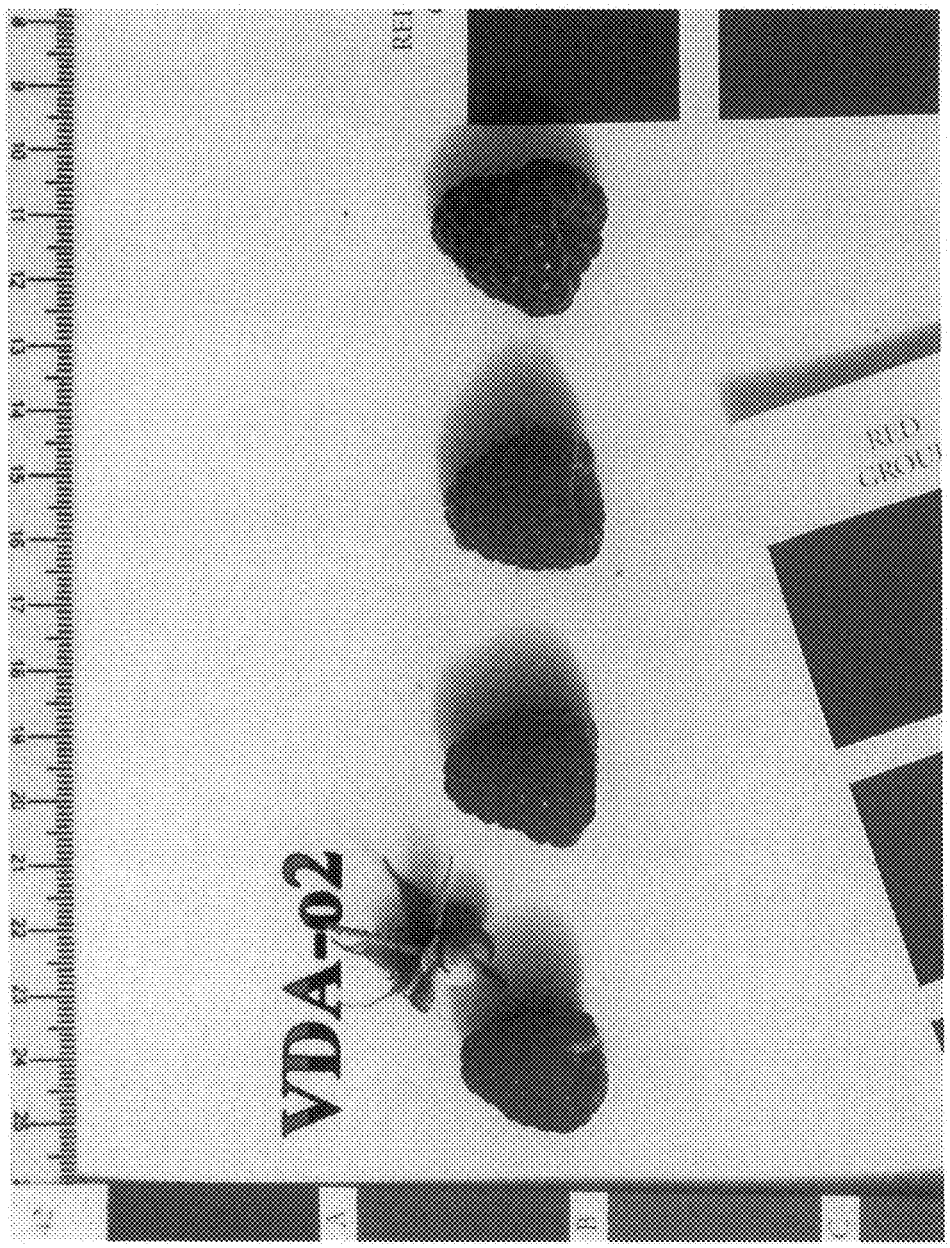

FIG. 6. shows a series of 'Addison' fruit from unripe and not harvestable on the left to commercial pick to ripe to overripe on the right; and 2001 Royal Horticultural Society Colour Plate Nos. 42 on left, 46 on bottom and 59 on the right.

Figure 7:
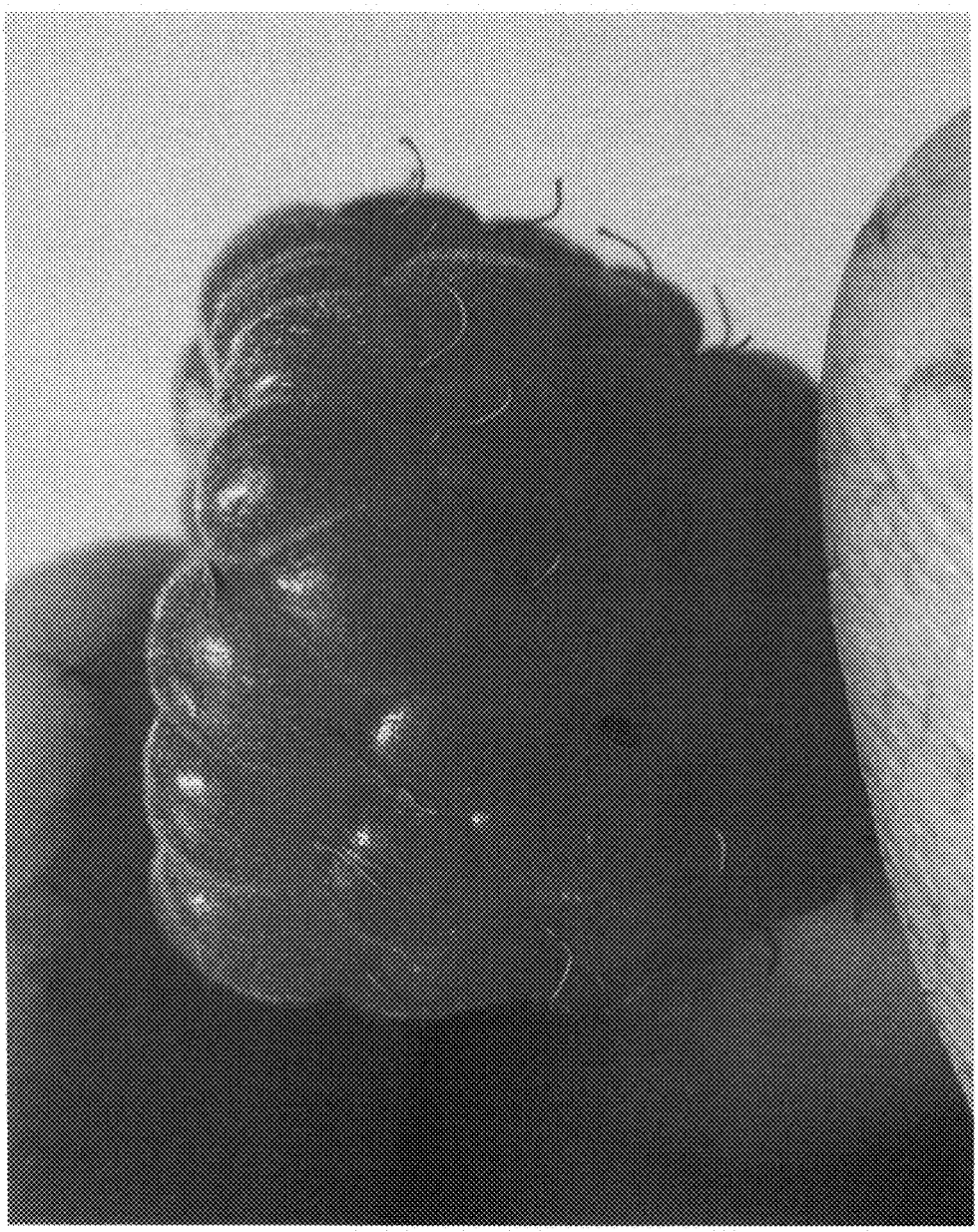

FIG. 7. shows an 'Addison' fruit and the dropped drupelet on the collar which causes a deformation of the fruit.

Figure 8:
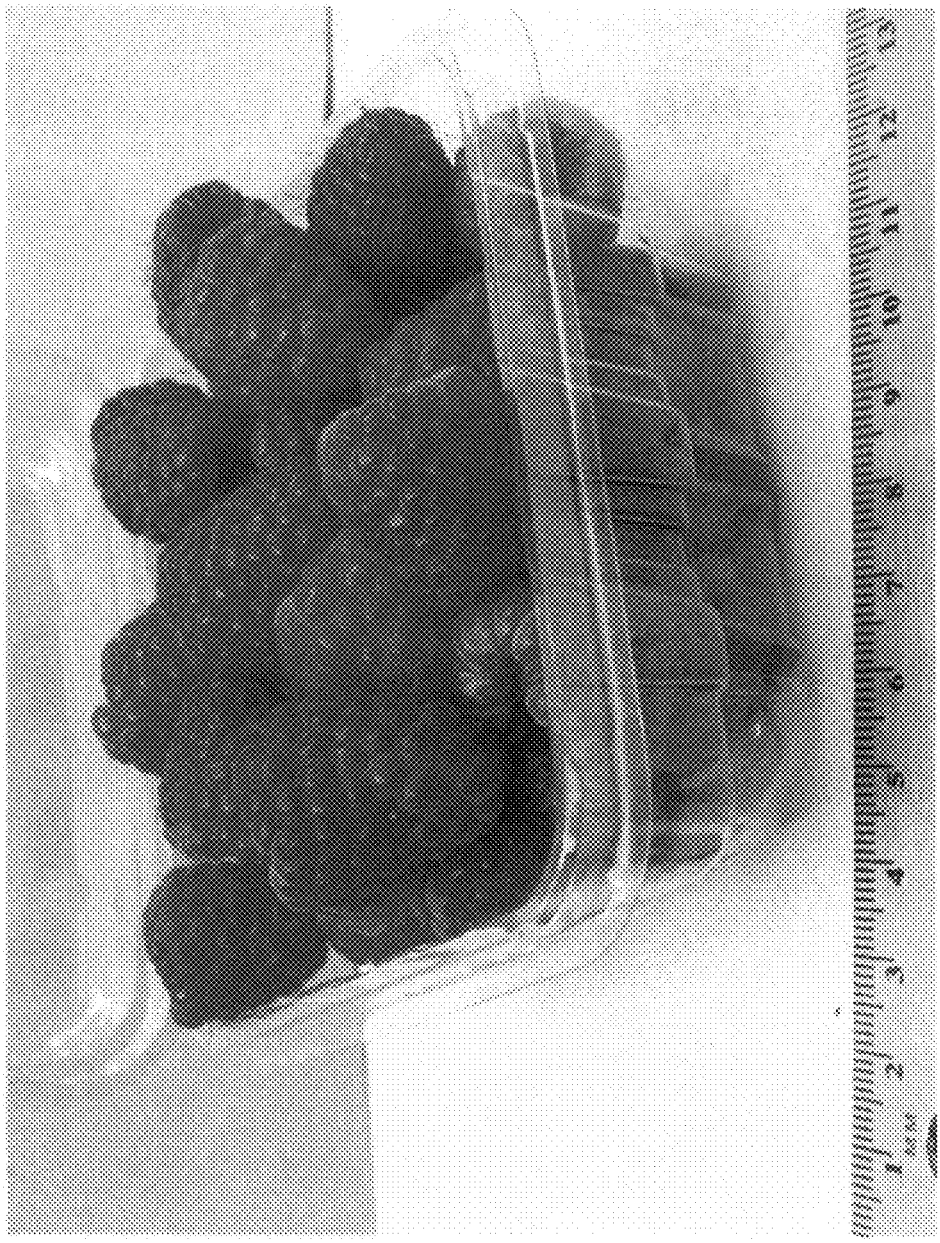

FIG. 8. shows early primocane fruit of 'Addison' immediately after picking in August.

Figure 9:
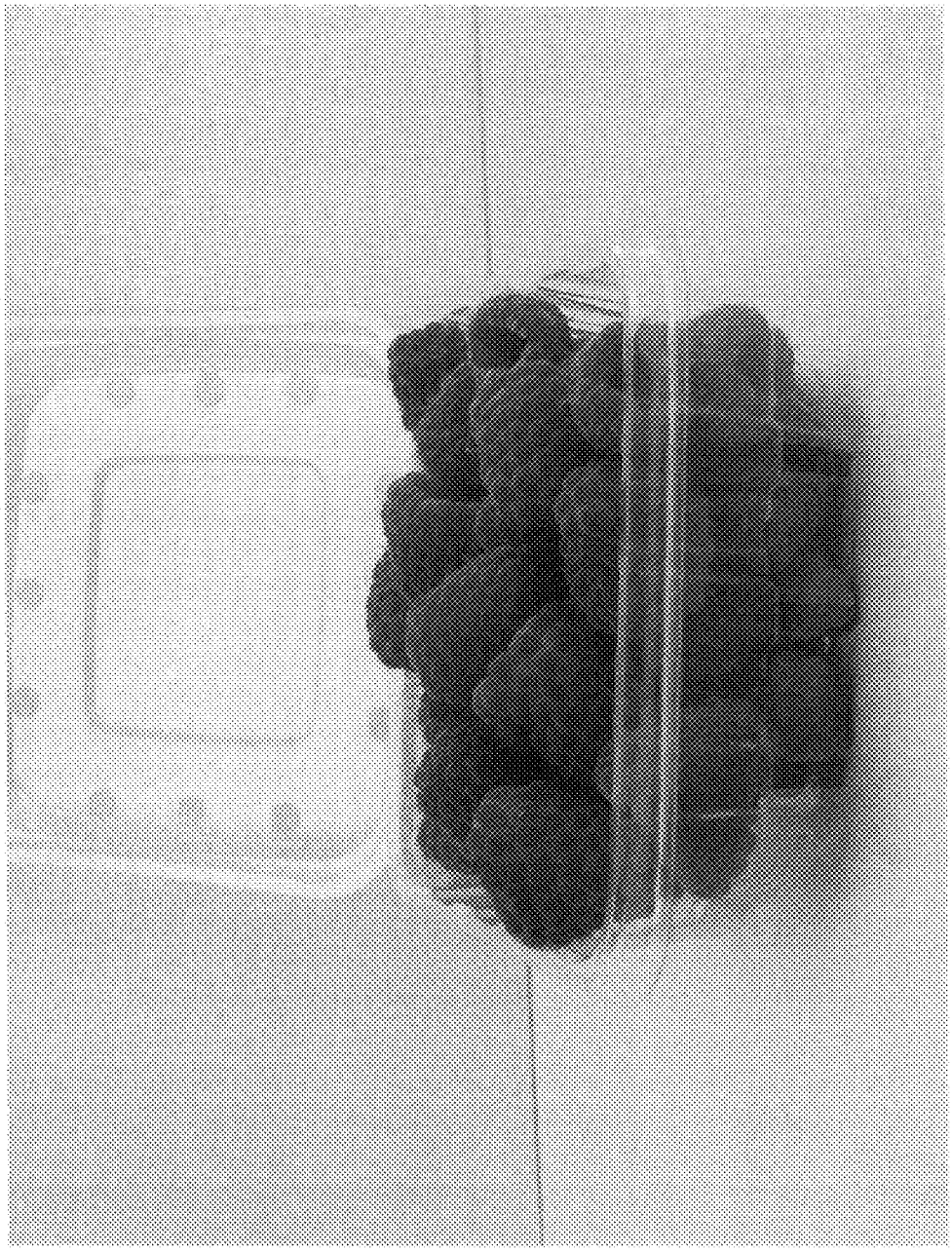

FIG. 9. shows the same fruit in FIG. 8 after 7 days of storage at 40° F.

DESCRIPTION OF THE NEW CULTIVAR

The following is a detailed description of 'Addison', the new cultivar, including fruit production, together with the cultivar's morphological characteristics. 'Addison' is a species hybrid, which contains a predominance of *Rubus idaeus* L. traits and would be botanically classified in that species commonly referred to as red raspberries. The description is based on information from 2 and 3 year old plants grown in tunneled fields at 2900 feet elevation in Oakland, Md. and in open fields in Wilmington, Ohio. As these climates differ, particularly in temperatures experienced in the growing season, we believe the description of 'Addison' will be consistent in other locations.

'Addison' produces a moderate number of root- and crown-suckers (approximately 19 per 10 gallon pot with a two year or older plant), more than 'Anne' (U.S. Plant Pat. No. 10,411) and 'Josephine' (U.S. Plant Pat. No. 12,173), similar to 'Marcianna' (U.S. Plant Pat. No. 21,007), but less than 'Caroline' (U.S. Plant Pat. No. 10,412) and 'Heritage' (unpatented). Young plants can produce more canes after the first flush, especially when the initial canes are removed or damaged. During the growing season, canes are light green colored, similar to 2001 Royal Horticultural Society Colour Plate No. 144B in spring and 144C in fall before leaf color changes (FIG. 1). 'Addison' canes are characterized by the large amount of red blush on all well lighted portions of the cane. The deep red blush is reminiscent of 2001 Royal Horticultural Society Colour Plate No. 182C in the spring and 183B in the fall (FIG. 2). Canes have a very light pubescence and very light waxiness. Field grown canes are usually stiffly semi-erect by the second year of a plant's growth, arching with the weight of primocane fruit. 'Addison' primocanes can branch vegetatively at the base of the original cane, typically up to 5 times; however, most canes on older plants (>88%) do not branch. Total node number per cane, including flowering nodes, averages 45.9 on first year tissue culture produced plants. By comparison, 'Heritage' (unpatented) produces 39 nodes per cane, 'Caroline' (U.S. Plant Pat. No. 10,412) produces 36 nodes per cane on tissue culture produced first year plants, 'Marcianna' (U.S. Plant Pat. No. 21,007) produces 40 nodes per cane and 'Josephine' (U.S. Plant Pat. No. 12,173) produces 48 nodes per cane. Vegetative growth is moderately vigorous, being terminated by floral development, reaching on average 65.8 inches in tunnels. Cane diameter at 30 cm. above ground averaged 0.95 cm. At the same location, internode length averaged 4.4 cm. Canes develop their normal woody color in the fall changing from green to the red blush color then to dark brown with approximately 20% of the cane area having lighter patches (2001 Royal Horticultural Society Colour Plate No. 177A to 177C). The base of 'Addison' dormant canes only slightly exfoliate, typically less than 3% of the area of the whole cane.

Thorns are many in density; ranging from 60 to 86 per internode, with an average of 69 at the base of the cane (FIG. 1); 0 to 17, with an average of 6.7 at mid cane height; on average 9.4 per internode in the floral section of the primocane. Thorn number on a peduncle averages 20.0 on primocanes and 12.3 on floricanes. Thorn shape is straight and needle-like and slightly downward pointing, to somewhat recurved downwards; full sized thorn length is approximately 4 mm. in length at the base of the cane to 2 mm. at the cane apex to, on average, 1 mm on peduncles. Thorn width at half height is less than 1 mm at the base of the cane to less than 0.5 mm on peduncles (FIGS. 1 and 3). 'Addison' thorn color is mostly grayed purple (2001 Royal Horticultural Society Colour Plate No. 183A) in color; including 1 mm. of the surrounding epidermis of the cane. This thorn coloration of the cane is in an oval oriented with the long axis parallel to the axis of the cane. By the last months of the growing season, the tip of the thorn becomes brown (2001 Royal Horticultural Society Colour Plate No. 177D). The color of the thorns turns completely brown (2001 Royal Horticultural Society Colour Plate No. 177D) in the dormant season, matching that of the overwintering floricanes. A similar pattern occurs with lateral buds, which turn cane-colored green to brown (2001 Royal Horticultural Society Colour Plate No. 177A) and are typical in size and shape of the species. Secondary buds were observed on less than 5% of the 'Addison' nodes, mostly at the mid and basal sections of the cane.

In late Spring, the lower surface of primocane 'Addison' leaves is pubescent grey-green resembling 2001 Royal Horticultural Society Colour Plate No. 191C becoming 194B in the fall. The upper surfaces of both primocane leaves are medium green, most closely in hue to 2001 Royal Horticultural Society Colour Plate No. 143A, depending on the amount of N fertilization and time of season. Petiole color, when unblushed, is reminiscent of 2001 Royal Horticultural Society Colour Plate No. 144B. Senescing leaves have a green yellow color resembling 2001 Royal Horticultural Society Colour Plate No. 146A. Leaves abscise readily in October and November. 'Addison' petioles, petiolules and the basal portion of the midribs of the leaves readily blush the same greyed-purple color resembling 2001 Royal Horticultural Colour Plates 183A and 183B, as found on canes (FIGS. 2 and 4). The extension of the color into the upper surface of the midrib is indicative of the cultivar if grown in well lighted conditions (FIG. 4).

'Addison' plants have leaves that are mostly trifoliolate with pentafoliolate leaves occurring on primocanes of vigorously growing older plants. In the floral section of the primocane, only trifoliolate and monofoliolate leaves occur (FIG. 5). Leaflet shape is oveate tapering to a point at the apical end and only very slightly cuneate at the base, if at all (FIGS. 2, 4 and 5). The trifoliolate terminal leaflet is, on average, 9.2 cm. wide and 13.4 cm. long on the base of the primocane, 6.0 cm. wide and 10.4 cm. long on the floral section of the primocane, and 5.8 cm. wide and 8.8 cm. long on spring floricane trusses. The trifoliolate maximum leaf width, measured from apex of the lateral leaflet to the opposite lateral leaflet apex is, on average, 21.6 cm. on the vegetative and 15.8 cm. on the floral sections of the primocanes respectively, and 13.1 cm. on average, on floricane truss leaves. The maximum width of the lateral leaflet for trifoliolate leaves averaged 6.1 cm. and 4.2 cm., on vegetative and floral portions of the primocane, respectively, and 4.0 cm. on floricane truss leaves. The trifoliolate leaf petiole and terminal petiolule lengths averaged 5.7 cm. and 3.3 cm. and 3.1 cm. and 2.4 cm. on vegetative and floral portions of the primocane, respectively, and 4.8 cm. and 1.8 cm. on floricane truss leaves. Thus the ratio of length of primocane leaves, including petiole and petiolule, to maximum leaf width is near 1 on primocanes but closer to 1.2 on floricanes. Lateral leaflets are sessile and join at the petiole apex with the apical leaf petiolule (FIGS. 2 and 4).

Monofoliolate leaves average 5.1 cm. in length and 2.0 cm in width. Petiole length averages 0.5 cm. On average, 3.3 monofoliolate leaves occur per floricane truss. In addition, small leaf bracts are found on peduncles, somewhat typical of 'Addison' (FIG. 3). Leaf serration is relatively simple and uniform sawtooth (FIG. 4). Leaves have moderately pronounced laminar puckering and typical red raspberry veination pattern. Leaf stipules are bladelike and average 0.7 cm in length in total; the basal one half of their length is fused to the petiole sides.

Flowers appear after 30.8 vegetative nodes, on average, on adult plant 'Addison' primocanes. By comparison, adult 'Marcianna' (U.S. Plant Pat. No. 21,007), 'Heritage' (unpatented) and 'Josephine' (U.S. Plant Pat. No. 12,173) primocanes flower, on average, after 23.8, 28.5 and 35.8 nodes respectively. Apical these vegetative nodes, 'Addison' primocane fruit appears on 15.2 nodes on average; thus, fruit is borne on 33% of the total nodes of the primocanes. The section of the primocane with fruit averages 16.7 inches in length. Based on nodes, the proportion of 'Addison' cane producing fruit is similar to 'Heritage' (27%) (unpatented), 'Caroline' (29%) (U.S. Plant Pat. No. 10,412), but higher than 'Josephine' (21%) (U.S. Plant Pat. No. 12,173) and less than 'Marcianna' (42%) (U.S. Plant Pat. No. 21,007). By observation in other fields, this proportion in 'Addison' is greater than that of 'Anne' (U.S. Plant Pat. No. 10,411), 'Autumn Bliss' (U.S. Plant Pat. No. 6,597), 'Autumn Britton' (unpatented), 'Amity' (unpatented), 'Crimson Giant' (U.S. Plant Pat. No. 23,375) or 'Ruby' (U.S. Plant Pat. No. 7,067).

The floral zone of the primocane is a compound cyme, which results from the terminal apex flowering and lateral flowers or trusses arising from subtending axillary buds on the cane (FIG. 5). Apical flowers are first to open on laterals and on the main cane. In 'Addison', the apical 1 to 5 lateral buds produce very short trusses and multiple fruit from unbranched or branched peduncles (FIG. 5). More basal buds produce elongated trusses with trifoliolate and monofoliolate leaves. The average number of flowers, arising from an axillary bud position on the primocane flower truss axis or main cane, from the apex, is: 1, 2, 2, 3, 4, 8, 5, 6, 6, 6, 6, 6, 5, 4, 1. The leafy laterals arising from the floral nodes are, on average, 7 nodes and 10 cm. in length. On average, 65 fruit are produced on the primocanes flower trusses.

Floricane flower trusses are typical cymose clusters; with 9.0 nodes bearing flowers apical to on average 3.5 nodes without flowers. Floricane trusses produce on average 17.4 flowers and are 44.7 cm. in length. Average peduncle length is 3.4 cm.

The unscented flower morphology and early fruit morphology is typical of most red raspberry cultivars, having five white (2001 Royal Horticultural Society Colour Plate No. 155D) petals that average 0.8 cm. long, 0.3 cm. wide on first opening flowers and 0.6 cm. long and 0.3 cm. wide on later flowers; petals abscise after pollination. Nectar production is copious, which can result in mold formation on flowers in tunnels. On average, early flowers have five 1.2 cm. long, 0.4 cm. wide at the base, triangular grey green sepals (2001 Royal Horticultural Society Colour Plate No. 144A) although some general sepal coloration can fade to yellow (2001 Royal Horticultural Society Colour Plate No. 161B) or red (2001 Royal Horticultural Society Colour Plate No. 180C). The sepals have two stripes of pubescence running along their outside length which lighten the color of the sepal from the inside to the sepal edge (2001 Royal Horticultural Society Colour Plate No. 143A to 143D), as is typical of red raspberries. 'Addison' sepal stripes are thinner than several cultivars. Sepals will sometimes roll lengthwise at the edges and will occasionally be unreflexed away from the fruit (FIG. 3). Fruit have green peduncles (2001 Royal Horticultural Society Colour Plate No. 191B) which have thorns and up to 2 reduced monofoliolate leaves reminiscent of bracts (FIG. 3). These bracts are approximately a cm. in length and occur on over 90% of the primocane fruit peduncles. The peduncle is noticeably more pubescent than the canes.

Early season floricane flowers have on average 60.8 pistils and a similar number of anthers, 57.4. These measured flowers develop, on average, into 3.0 gram fruit, which averaged 2.50 cm long and 1.98 cm wide with a cavity of 0.84 cm in diameter. Early season primocane flowers have, on average, 55.6 pistils and 87.7 anthers. These measured flowers develop, on average, into 3.9 gram fruit, which averaged 2.34 cm in width and 2.05 cm in width with a cavity diameter of 0.96 cm. Drupelet size is medium. Anther and pistil color is similar to Royal Horticultural Society Color Plate No. 157A; none of these traits can be used to identify 'Addison'.

FRUIT PRODUCTION

'Addison' Spring fruit size and weight are moderately large, and reduce in size as ripening progresses down individual trusses or truss laterals. Early floricane fruit averaged 3.3 grams in weight but the last harvests averaged 2.2 grams. The initial, or early primocane fruit ripening is staggered on different canes because the conversion of vegetative growth to flowering does not occur on all canes as uniformly as in floricanes; which are well timed when given winter chilling over 1000 hours. Over the entire season in a planting, there was no consistent reduction in fruit size except after 90% harvest. Primocane fruit averaged 3.33 grams on older plants and 3.44 grams on tissue culture plants.

The fruit receptacle remains on the plant after harvest and is slightly wider at its mid-point. However, this causes no distension or breakage of the fruit at harvest as the receptacle neck is elongate, averaging one third of the total length of the receptacle, and fruit attachment occurs only on the area of the receptacle which is conic, getting smaller toward the apex (FIG. 5). Thus, fruit is detached smoothly, once the vascular connections are freed during ripening. The receptacle is cream yellow at ripeness, reminiscent of Royal Horticultural Society Color Plate No.158D and it remains on the plant after fruit harvest. The apical tip of the receptacle will typically darken shortly after fruit harvest (FIG. 5). 'Addison' fruit are cohesive, unless pollination problems exist, the fruit does not otherwise shatter under pressure of hand harvest.

August flowering fruit ripens 29 days after pollination on primocanes in a tunnel in Oakland, Md. In tunnels and in potted culture, floricane fruit was 5% ripe on May 22, 2014, 50% ripe on Jun. 4, 2014 and 95% ripe on Jun. 18, 2014. Primocane fruit was 5% ripe on Aug. 8, 2014, 50% ripe on September 2 and 95% ripe on Sep. 20, 2014. In 2015, on first year tissue culture plants, primocane fruit ripened beginning July 30, but 5% ripe did not occur until August 13, 50% ripe occurred on September 25 and 95% ripe occurred on October 21. First year plants are typically later to produce fruit on primocanes on all raspberry cultivars observed, thus, the difference in primocane ripening season of older (2014) vs. first year (2015) plants is not unusual to 'Addison'.

'Addison' primocane and floricane fruit undergo a progressive darkening from unripe to ripe to stored overripe. Under-ripe fruit, which cannot be picked without shattering, closely resembles the hue of 2001 Royal Horticultural Society Colour Plate No. 42B (FIG. 6). At easily picked for commercial shipping and storage, the now very firm red fruit resemble 2001 Royal Horticultural Society Colour Plate No. 46B. At full ripe, fruit color is 2001 Royal Horticultural Society Colour Plate No. 46A and upon softening, 2001 Royal Horticultural Society Colour Plate No. 59A. Upon 7 days storage, fruit develops a darker red color, resembling 2001 Royal Horticultural Society Colour Plate No. 79A. Fruit at this stage can be handled without collapsing.

Fruit are moderately glossy at harvest but become less glossy, duller on storage. Fruit have a slight amount of observable pubescence which become more noticeable on storage. Drupelet arrangement has a typic fault; the uniform top row of drupelets will have a single drupelet "drop" to half way to the second row (FIG. 7). This results in an angular defect in the otherwise uniform collar. This defect can result in a flatter than normal face to one side of the fruit. Except when picked unripe, the fruit does not crack upon harvest because of this defect.

Commercially picked fruit does not break down after at least one week in common storage at 40° F. (FIGS. 8 and 9); however, 'Addison' is not resistant to spotted wing *drosophila* (*Drosophila suzukii*) and fruit will collapse if inhabited by one or more maggots. During high populations of the fruit fly and with no pesticide or fly controls used, up to 40% of fruit will not collapse after storage.

Fruit at ripe stage, has 10.1% soluble solids (degrees Brix) by refractometer. Flavor is sweet and remains so during unfavorable weather. The original selection of VDA-o2 was made based on its sweetness under extraordinary drought conditions in Ohio. 'Addison' floricanes have only average resistance or hardiness to fluctuating early spring temperatures where tested. Floricanes are otherwise hardy to zone 6 of the U.S. Dept. of Agriculture classifications.

'Addison' has been yield tested in a tunnel in Oakland, Md. The following data were collected in >2 year old potted plants in the Summer and Fall of 2014. 'Addison' averaged 1200.1 grams per plant from floricanes and 737.5 grams per plant in the primocane season. In 2015, potted tissue culture plants had primocane yields ranging between 597 and 1057, and on average, 759.3 grams per plant. At the spacing used in these measurements, a yield of 1000 grams per plant would be equivalent to 8000 lbs. per acre or 9000 kg. per hectare.

The plant is slightly susceptible to late season leaf rust (yellow rust). The plant's reaction to *Phyophthora fragariae* var. rubi root rot is evidently moderately resistant, based on field reaction, not on controlled testing. When plants were excessively watered in pots in a glasshouse, symptoms of *Phytophthora fragariae* var. rubi were not observed, while other genotypes succumbed to this root rot and had *Phytophthora* sp. isolated from their infested tissues. However, the plant will not tolerate planting in areas with standing water for up to a week. Fruit is usually free from *Botrytis* rot in unsprayed protected tunnels, more so than 'Anne' (U.S. Plant Pat. No. 10,411) and 'Caroline' (U.S. Plant Pat. No. 10,412), and similar to 'Josephine' (U.S. Plant Pat. No. 12,173).

'Addison' can be asexually propagated by tissue culture or by root suckers. Tissue culture methods include the use fo sodium hypochlorite surface disinfested lateral vegetative buds for initiation. Benzyl amino purine (0.3 mg per liter) was used to force non-adventitious shoot branching for division propagation. Shoots were rooted with iadole butyric acid in vitro. Plants produced in laboratories in Oakland, Md. and Lacota, Mich. were identical to the original selection. No off-type plants have been observed in the history of asexual propagation of this cultivar by either method.

What is claimed:

1. A new and distinct spring and fall bearing, dark fruited, red raspberry plant known as 'Addison' as described herein, illustrated and identified by the characteristics set forth above.

* * * * *